(12) United States Patent
Kärcher et al.

(10) Patent No.: US 12,414,812 B2
(45) Date of Patent: Sep. 16, 2025

(54) CONNECTING DEVICE AND MONOPOLAR CABLE FOR MONOPOLAR AND BIPOLAR OPERABLE SURGICAL INSTRUMENTS, SURGICAL INSTRUMENT AND SURGICAL SYSTEM

(71) Applicant: KARL STORZ SE & Co KG, Tuttlingen (DE)

(72) Inventors: Daniel Kärcher, Tuttlingen (DE); Jochen Stefan, Tuttlingen (DE); Tobias Unger, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 887 days.

(21) Appl. No.: 17/531,604

(22) Filed: Nov. 19, 2021

(65) Prior Publication Data

US 2022/0160420 A1    May 26, 2022

(30) Foreign Application Priority Data

Nov. 20, 2020 (DE) .......................... 102020130716.0

(51) Int. Cl.
*A61B 18/14* (2006.01)
*A61B 18/00* (2006.01)
*A61B 18/12* (2006.01)

(52) U.S. Cl.
CPC ...... *A61B 18/1445* (2013.01); *A61B 18/1206* (2013.01); *A61B 2018/00077* (2013.01); (Continued)

(58) Field of Classification Search
CPC ............ A61B 18/1445; A61B 18/1206; A61B 2018/00077; A61B 2018/00083;
(Continued)

(56) References Cited

U.S. PATENT DOCUMENTS 4,244,371 A     1/1981   Farin
5,573,424 A * 11/1996   Poppe .................... A61B 18/14
                                                                                                                                                 439/502
(Continued)

FOREIGN PATENT DOCUMENTS

DE       2514501        10/1976
DE       2646229 A1     4/1978
(Continued)

OTHER PUBLICATIONS

Schenkl, German Search Report, Jul. 29, 2021, pp. 1-8, DPMA, Munich.
(Continued)

*Primary Examiner* — Linda C Dvorak
*Assistant Examiner* — William Mossbrook
(74) *Attorney, Agent, or Firm* — David N. Villalpando; Jacqueline Cohen

(57) ABSTRACT

The present invention relates to a connecting device and to a monopolar cable for surgical instruments operable in a monopolar and bipolar manner, especially for high-frequency surgery, and a corresponding surgical instrument and surgical system. An electrical terminal of the connecting device is designed to be connectable either to a monopolar cable for monopolar operation or to a bipolar cable for bipolar operation. A first contact and a second contact of the electrical terminal are electrically connected to an accessory coupling of the connecting device and are designed with insulation such that an accessory coupled by the accessory coupling is operable either in a monopolar or bipolar manner via the two contacts. The present invention further relates to a monopolar cable for such a connecting device, to a surgical instrument comprising such a connecting device and to a surgical system comprising such a surgical instrument and such a monopolar cable.

19 Claims, 4 Drawing Sheets

(52) U.S. Cl.
CPC .............. *A61B 2018/00083* (2013.01); *A61B 2018/00178* (2013.01); *A61B 2018/00607* (2013.01); *A61B 2018/1253* (2013.01); *A61B 2018/126* (2013.01)

(58) Field of Classification Search
CPC ........... A61B 2018/00178; A61B 2018/00607; A61B 2018/1253; A61B 2018/126; A61B 18/1442; A61B 2017/0046; A61B 2017/00464; A61B 2017/00477; A61B 18/1402; A61B 2018/00589; A61B 2018/00595; A61B 2018/0091; A61B 2018/146; A61B 2018/1495
See application file for complete search history.

(56) References Cited

U.S. PATENT DOCUMENTS

| | | | |
|---|---|---|---|
| 6,113,596 A | 9/2000 | Hooven et al. | |
| 6,402,747 B1 * | 6/2002 | Lindemann | A61B 18/1445 606/45 |
| 9,662,164 B1 * | 5/2017 | Kirwan, Jr. | H01R 27/00 |
| 11,564,740 B2 | 1/2023 | Cosmescu | |
| 2002/0151890 A1 * | 10/2002 | Scholer | A61B 18/1445 606/46 |
| 2005/0113827 A1 | 5/2005 | Dumbauld et al. | |
| 2011/0319883 A1 | 12/2011 | Farin | |
| 2012/0202388 A1 * | 8/2012 | Selig | A61B 18/14 439/656 |
| 2014/0316401 A1 * | 10/2014 | Crews | A61B 34/37 606/34 |
| 2019/0298444 A1 * | 10/2019 | Xu | A61B 1/04 |

FOREIGN PATENT DOCUMENTS

| | | | | |
|---|---|---|---|---|
| DE | 20107483 | U1 * | 1/2002 | ............ A61B 18/14 |
| DE | 112017005056 | T5 | 6/2019 | |
| EP | 0338105 | A1 | 10/1989 | |
| EP | 2405845 | B1 | 6/2014 | |
| EP | 2842509 | A1 | 3/2015 | |
| EP | 3005968 | B1 | 5/2017 | |
| EP | 2928400 | B1 | 12/2020 | |

OTHER PUBLICATIONS

Schmidt, Matthias, Extended European Search Report, Apr. 4, 2025, pp. 1-8, European Patent Office, Munich.

* cited by examiner

CONNECTING DEVICE AND MONOPOLAR CABLE FOR MONOPOLAR AND BIPOLAR OPERABLE SURGICAL INSTRUMENTS, SURGICAL INSTRUMENT AND SURGICAL SYSTEM

CROSS REFERENCE TO RELATED APPLICATIONS

This application claims priority to German Patent Application No. 102020130716.0, filed Nov. 20, 2020, and entitled, "Verbindungsvorrichtung und monopolares Kabel für mono-polar und bipolar betreibbare chirurgische Instrumen-te, chirurgisches Instrument und chirurgisches System," or "Connecting device and monopolar cable for monopolar and bipolar surgical instruments, surgical instrument and surgical system" and is incorporated herein by reference.

TECHNICAL FIELD OF THE INVENTION

The present invention relates to a connecting device for surgical instruments operable in a monopolar and bipolar manner, especially for high-frequency surgery (HF surgery), and to a corresponding monopolar cable and to a corresponding surgical instrument operable in a monopolar and bipolar manner and to a corresponding surgical system.

BACKGROUND OF THE INVENTION

Surgical instruments often have a connecting device, especially a handle or a robot interface, and a tool usually referred to as accessory which can be attached thereto by means of an accessory coupling, for example shears, a clamp or the like.

In high frequency (HF) surgery, in what is called electrotomy (also called diathermy or electrocautery) and in coagulation, the thermal effect of high-frequency AC current on tissue is exploited in order to sever target tissue and, if appropriate, to stem bleeding simultaneously or instead. For this purpose, the surgical instruments have one or more (active) electrodes on their accessory (e.g., clamp, shears or the like), via which the high-frequency AC current is introduced into a patient's target tissue. For the desired effect of electrotomy and/or coagulation to occur in the target tissue, a high current density is introduced in the target tissue. Therefore, (active) electrodes generally have a small surface area and, for example, have a needle-like or blade-like design for this purpose, in order to introduce the high-frequency AC current supplied into the target tissue with maximum current density. It is possible here to use surgical instruments operated either in a monopolar or bipolar manner.

In the case of surgical instruments operated in a monopolar manner, a single active electrode is disposed on the accessory of the surgical instrument, via which the high-frequency AC current is introduced into a patient's tissue. For the current to be able to be introduced into the tissue from the single active electrode, it is necessary to mount a large-area counterelectrode (neutral electrode) on the patient's body as opposite pole.

In the case of surgical instruments operated in a bipolar manner, two electrodes (active electrode and neutral electrode) are disposed on the accessory of the surgical instrument. In this case, the high-frequency AC current is introduced into the target tissue from a first electrode (active electrode) directly opposite the second electrode (neutral electrode).

In order to achieve the desired effect (electrotomy and/or coagulation) in the target tissue, higher voltages are required between the active electrode on the accessory and the large-area neutral electrode on the patient's body in the case of surgical instruments operated in a monopolar manner than between the two electrodes on the tool in the case of surgical instruments operated in a bipolar manner. Thus, in connecting devices, especially in handles, of surgical instruments operated in a monopolar manner, greater isolation gaps and leakage gaps have to be provided than in the case of surgical instruments operated in a bipolar manner. A connecting device or handle of a surgical instrument operated in a bipolar manner therefore cannot be used for surgical instruments operated in a monopolar manner since there may otherwise be malfunctions and short circuits. It is likewise impossible to use a handle of a surgical instrument operated in a monopolar manner for a surgical instrument operated in a bipolar manner.

In order to avoid confusion in the connection of surgical instruments to an HF generator, plugs and sockets on the handles and cables are typically in each case shape-coded, such that monopolar cables can be connected only to handles of surgical instruments operated in a monopolar manner, and bipolar cables only to handles of surgical instruments operated in a bipolar manner.

SUMMARY OF THE INVENTION

Against this background, it is an object of the present invention to provide an improved and, in particular, more flexibly usable connecting device and a monopolar cable for surgical instruments operable in a monopolar and bipolar manner.

According to the invention, this object is achieved by a connecting device, as well as by a monopolar cable, a surgical instrument and a surgical system having the features described below.

A connecting device for surgical instruments operable in a monopolar and bipolar manner, especially for high-frequency surgery, comprises a housing, an accessory coupling and an electrical terminal. The accessory coupling is disposed on the housing. The accessory coupling is designed for mechanical and electrical coupling of an accessory operable in a monopolar manner and additionally or alternatively in a bipolar manner. The electrical terminal is disposed on the housing. The electrical terminal has a first contact and a second contact. The electrical terminal is designed to be connectable either to a monopolar cable (for monopolar operation) or to a bipolar cable (for bipolar operation). The first contact and the second contact are designed to be electrically connected to the accessory coupling and isolated in such a way that an accessory coupled by the accessory coupling is operable either in a monopolar or bipolar manner via the two contacts.

The concept underlying the present invention is, by means of the two contacts executed with sufficient insulation from one another and electrical connections of these two contacts to the accessory coupling, to design a surgical instrument equipped with the connecting device according to the invention so as to be operable either in a monopolar or bipolar manner.

The surgical instrument operable in a monopolar and bipolar manner is used in surgical interventions. Especially in high-frequency surgery, it is possible to use the surgical instrument operable either in a monopolar or bipolar manner to sever tissue (electrotomy) and additionally or alternatively to stem bleeding (coagulation). The surgical instrument operable in a monopolar and bipolar manner may, for example, be an instrument guided manually by a user or operator (e.g. surgeon) or one guided by a robot (arm).

The connecting device is designed such that it can be used to guide a mechanically connected accessory. More particularly, it is possible for example for a user (e.g. surgeon) to hold a guide element executed as a handle in their hand and hence to guide a mechanically connected accessory manually. In addition, for example, a connecting device executed as a manipulator coupling or robot receptacle may be connected to a surgical robot, and hence a mechanically connected accessory can be guided by the surgical robot.

The housing may be executed in integral or one-piece form, or be formed from multiple components (e.g., shell elements) mechanically connected to one another in a detachable or fixed manner. The housing may be manufactured at least partly from a plastic, a metal or an alloy. The housing may preferably be manufactured at least partly from a biocompatible material. The housing may be mechanically connected to the accessory coupling in a detachable or fixed manner. Alternatively, the housing may accommodate the accessory coupling. Further in the alternative, the housing may encompass the accessory coupling or be designed integrally therewith. The housing may be mechanically connected to the electrical terminal in a detachable or fixed manner. Alternatively, the housing may accommodate the electrical terminal. Further in the alternative, the housing may encompass the electrical terminal or be designed integrally therewith.

The accessory coupling is executed in such a way that the accessory operable in a monopolar manner and additionally or alternatively in a bipolar manner (e.g., shears, clamp or the like) is mechanically connectable to the housing in a detachable manner (mechanical coupling). For example, the accessory coupling may be designed as an inner thread, outer thread, bayonet adapter (bayonet coupling), snap element (snap connection), especially radially sprung ring, or the like, which may be connected in a mechanically detachable manner to a matching counterpart at a proximal end of the accessory. In addition, the accessory coupling is executed in such a way that an electrical connection exists between the detachably mechanically connected accessory and the accessory coupling (electrical coupling). The electrical connection may be implemented via a plug-socket connection, contact plates, sliding contacts and the like. By means of the electrical coupling, the accessory is electrically connected to the first contact and the second contact of the electrical terminal. For this purpose, suitable wires from the accessory coupling may run along the inside or outside of the housing to the electrical terminal and electrically connect these to one another.

The electrical terminal is designed such that the monopolar or bipolar cable is connectable to a suitable electrical terminal element (on the connecting device side). It is thus possible for the monopolar/bipolar cable, via its suitable electrical terminal element, especially on the connecting device side, to be firstly detachably mechanically connected to the electrical terminal and secondly electrically connected to the first contact and additionally or alternatively to the second contact. For example, the electrical terminal may be designed as a plug, socket, inner thread, outer thread, bayonet adapter, snap element, especially radially sprung ring, or the like, with integrated first and second contact.

The electrical terminal comprises the first and second contacts. The first contact and additionally or alternatively the second contact may be manufactured at least partly from an electrically conductive material, preferably stainless steel, gold, platinum, copper, aluminium, tungsten or the like, and combinations thereof. More particularly, the first contact and additionally or alternatively the second contact may be manufactured from stainless steel with a gold coating. Via the first contact and additionally or alternatively via the second contact, it is firstly possible for the one pole of a monopolar cable to be electrically connected to the electrical terminal. Secondly, via the first contact and the second contact, it is possible for the two poles of a bipolar cable to be electrically connected to the electrical terminal. The one pole/two poles of the monopolar/bipolar cable may be electrically connected to the accessory coupling via the suitable wires. The first electrical contact and the second electrical contact here are isolated in such a way that, both in the case of bipolar operation with two different poles electrically connected to the first and second contacts and in the case of monopolar operation with a single pole electrically connected to the first contact and additionally or alternatively to the second contact, no electrical current can flow between the two contacts and between any of the contacts and their environment. Preferably, the first contact and second contact are executed with isolation such that a voltage of 0 V [volts] to 5500 V in monopolar operation and a voltage of 0 V to 1000 V in bipolar operation, further preferably a voltage of 0 V to 4300 V in monopolar operation and a voltage of 0 V to 250 V in bipolar operation, and more preferably a voltage of 0 V to 3000 V in monopolar operation and a voltage of 0 V to 190 V in bipolar operation may be present, without resulting in any short circuit or flashover. Moreover, voltage security can be assured to an even higher degree, especially also with values, the application of which is approved for the particular user.

The connecting device according to the invention allows rapid switching, with low complexity, between an accessory operable in a monopolar manner and an accessory operable in a bipolar manner, or between monopolar operation and bipolar operation. It is not necessary to switch between a connecting device for monopolar operation and one for bipolar operation. It is thus possible for the user (e.g. surgeon) to switch quickly and easily between monopolar and bipolar operation during a surgical intervention. This reduces the time taken for surgical interventions and hence the risk for patients. In addition, the number of parts to be cleaned after the surgical intervention is reduced.

Advantageous configurations and developments will be apparent from the further subordinate embodiments and from the description with reference to the figures of the drawing.

In one development of the present invention, a contact insulation for electrical isolation of the first contact and the second contact from one another is provided. The contact insulation electrically isolates the first contact from the second contact. In addition, the contact insulation isolates the first contact and the second contact from their environment. Only in a respectively predefined region are the first contact and the second contact not electrically isolated from their environment, such that the electrical connection can be established there with the monopolar or bipolar cable or with the one pole or both poles thereof.

The contact insulation may be manufactured at least partly from a plastic or a ceramic.

In one embodiment, the contact insulation is formed by at least one tube, especially shrink tube. Additionally or alternatively, the contact insulation may be formed by at least one coating. Additionally or alternatively, the lead insulation may be formed by at least one tube made of polyetheretherketone (PEEK). The contact insulation encloses the first contact and additionally or alternatively the second contact. The contact insulation enables selective monopolar or bipolar operation of the surgical instrument since a short circuit in both modes of operation is effectively prevented.

In one development, a first power lead for electrical connection of the first contact and a second power lead for electrical connection of the second contact to the accessory coupling are disposed in or on the housing. A lead insulation for electrical isolation of the first power lead and of the second power lead from one another and from their environment is provided.

The first power lead connects the first contact of the electrical terminal to the accessory coupling. It is thus possible to electrically connect one pole of a monopolar or bipolar cable connected to the electrical terminal to the accessory operable in a monopolar or bipolar manner, coupled to or with the accessory coupling.

The second power lead connects the second contact of the electrical terminal to the accessory coupling. It is thus possible to electrically connect the same pole or a further pole of a monopolar or bipolar cable connected to the electrical terminal to the accessory operable in a monopolar or bipolar manner, coupled to or with the accessory coupling.

The first power lead and additionally or alternatively the second power lead may be manufactured at least partly from an electrically conductive material, preferably stainless steel, gold, platinum, copper, aluminium, tungsten or the like, and combinations thereof. More particularly, the first power lead and additionally or alternatively the second power lead may be manufactured from stainless steel with a gold coating.

The lead insulation electrically isolates the first power lead from the second power lead. In addition, the lead insulation isolates the first power lead and the second power lead from their environment. In one embodiment, this corresponds to a shaft isolation from the outside. More particularly, an isolation here does not have any isolating effect from the outside between the poles.

The lead insulation may be manufactured at least partly from a plastic or a ceramic.

In one embodiment, the lead insulation is formed by at least one tube, especially shrink tube. Additionally or alternatively, the lead insulation is formed by at least one coating. Additionally or alternatively, the lead insulation is formed by at least one tube that especially contains plastic, preferably PEEK. The lead insulation surrounds the first power lead and additionally or alternatively the second power lead.

The lead insulation enables selective monopolar or bipolar operation of the surgical instrument, since a short circuit is effectively prevented in both modes of operation. More particularly, a short circuit is effectively prevented between the first power lead and second power lead in bipolar operation, and between the first or second power lead and the environment thereof in monopolar and bipolar operation. This is especially also advantageously ensured in the case of a neutral electrode provided on the patient in operation.

In one development of the present invention, the contact insulation and additionally or alternatively the lead insulation has an isolation gap designed for AC currents in monopolar operation, preferably for coagulation and additionally or alternatively electrotomy.

The contact insulation and additionally or alternatively the lead insulation is designed such that, in the case of monopolar operation with AC current, especially with a voltage of 0 V to 5500 V, preferably of 0 V to 4300 V and more preferably of 0 V to 3000 V, no measurable current flows between the first contact and the second contact and between these and their environment, or between the first power lead and the second power lead and between these and their environment. Moreover, the contact insulation and additionally or alternatively the lead insulation is designed such that, in the case of monopolar operation with AC current, especially with a voltage of 0 V to 5500 V, preferably of 0 V to 4300 V and more preferably of 0 V to 3000 V, no measurable leakage current flows at the surface thereof. An unwanted short circuit or flashover can thus be prevented in a particularly reliable manner both in the case of bipolar operation and in the case of monopolar operation of the surgical instrument.

In one development of the present invention, the electrical terminal is designed for selective connection of the first contact and of the second contact to a monopolar cable or to a bipolar cable via a common plug.

The common plug enables contact connection between the one pole of the monopolar cable or the two poles of the bipolar cable and the first contact and the second contact via a single element, for example a pin. At the same time, the common plug establishes the mechanical connection between the electrical terminal of the connecting device and the suitable electrical terminal element of the monopolar or bipolar cable on the connecting device side by static friction. The static friction is established via a transition fit or interference fit, with the additional possibility of establishing static friction via elastic elements. Additionally or alternatively, the mechanical connection can be established by means of a ball catch, a snap ring or the like. By means of the common plug, it is possible in a particularly simple manner to establish the mechanical and electrical connection between the electrical terminal and the suitable electrical terminal element on the connecting device side.

In one development, the electrical terminal takes the form of the common plug. The common plug has, on its outer surface, in its longitudinal direction, the first contact in a first contact region, the contact insulation in an insulation region, and the second contact in a second contact region.

The electrical terminal of the connecting device, in the form of the common plug, may form electrical contact in the first contact region either with the one pole of the monopolar cable or with one of the two poles of the bipolar cable. In the second contact region, it is likewise correspondingly possible to form electrical contact either with the one pole of the monopolar cable or with the other of the two poles of the bipolar cable.

The electrical terminal in the form of the common plug, after a surgical intervention, can be cleaned and sterilized in a particularly simple manner together with or separately from the connecting device.

In one development of the present invention, the electrical terminal takes the form of a common socket. The common socket has, on its inner surface, in its longitudinal direction, the first contact in a first contact region, the contact insulation in an insulation region, and the second contact in a second contact region.

The electrical terminal of the connecting device designed as the common socket may, in the first contact region, form electrical contact either with the one pole of the monopolar cable or with one of the two poles of the bipolar cable. In the second contact region, it is likewise correspondingly possible to form electrical contact either with the one pole of the monopolar cable or with the other of the two poles of the bipolar cable.

The electrical terminal in the form of the common socket is particularly protected from mechanical deformations since there is no outward protrusion of any contact element (e.g., pin) and hence there is also no possibility of unintentional bending.

In one development of the present invention, an actuating element is also disposed on the housing. A drive is disposed in or on the housing. The drive is mechanically coupled to the actuating element. The drive is designed for transmission of a movement of the actuating element to a mechanism of an accessory which is mechanically connectable via the accessory coupling, especially with a predetermined transmission.

The housing may be detachably or non-detachably mechanically connected to the actuating element, with the actuating element being movable or rotatably mounted in at least one translational and additionally or alternatively rotational degree of freedom with respect to the housing. The drive is mounted so as to be movable within an interior of the housing or on the outside thereof such that a shift or rotation in at least one translational and additionally or alternatively rotational degree of freedom with respect to the housing is possible.

The actuating element serves for introduction of force or torque and transmission of force or torque from the outside. The actuating element may be designed, for example, as a manual control by means of which a user or operator (e.g. surgeon) can manually introduce a force for actuation of an accessory, or as an actuation coupling for a robot (arm).

The drive is mechanically connected to the actuating element and absorbs force or torque introduced via the actuating element from the outside and passes it onward to the mechanism of the connected accessory in the region of the accessory coupling. It is possible here for a force introduced by the actuating element to be converted to a torque, or torque introduced to be converted to a force. It is thus possible to convert a rotation to a translation and vice versa. The drive can also be used to implement a transmission with a predefined transmission ratio between the actuating element and the mechanism of the connected accessory or a manipulator of the accessory, which is actuated via the mechanism of the accessory.

For example, the actuating element may be designed as a rotatable grip of a pair of shears and the drive as a drive rod mounted so as to be translationally movable in a sliding sleeve in the housing. The grip of the pair of shears may lie on a correspondingly shaped sliding surface at a proximal end of the drive rod, such that a rotational movement of the grip of the pair of shears is transmitted to the drive rod and converted to a translation.

By means of the actuating element and the drive, it is possible for different accessories with different manipulators (e.g., shears, clamp etc.) to be coupled to and actuated via the connecting device.

In one development of the present invention, the drive is designed to be at least partly electrically conductive. The drive at least partly forms either the first power lead and additionally or alternatively the second power lead.

The drive is used to electrically connect the first contact and additionally or alternatively the second contact of the electrical terminal to the accessory coupling. For example, the drive designed as a drive rod mounted in the sliding sleeve may at least partly form the first power lead via said drive rod. Said drive rod is electrically connected via a sliding contact to the first contact of the electrical terminal. Additionally or alternatively, the sliding sleeve may form at least part of the lead insulation, for example in the form of a sleeve of polytetrafluoroethylene (PTFE), and at the same time form at least partly the second power lead. For this purpose, a conductive sleeve electrically connected to the second contact of the electrical terminal may be arranged around the (inner) portion of the sliding sleeve that forms the lead insulation.

In this way, it is possible to establish the electrical connection between the accessory and the monopolar or bipolar cable via the connecting device with particularly few elements in a very efficient and simple manner.

In one development of the present invention, the accessory coupling is designed for mechanical and electrical coupling of an accessory in the form of a clamp or shears.

In one development of the present invention, the contact insulation and additionally or alternatively the lead insulation each have an isolation gap designed for AC currents with a voltage of up to 5.5 kV [kilovolts], preferably up to 4.3 kV and more preferably up to 3.0 kV.

In the case of monopolar operation, especially in electrosurgery, AC currents with a voltage of up to 5500 V or 5.5 kV are used. By virtue of the contact insulation and additionally or alternatively the lead insulation, any unwanted short circuit or flashover between the first contact and the second contact or between the first power lead and the second power lead is effectively prevented.

Another aspect of the invention includes a monopolar cable for surgical instruments operable in a monopolar and bipolar manner, especially for high-frequency surgery, comprises an electrical terminal element on the generator side, an electrical terminal element on the connecting device side, and a bridge. The electrical terminal element on the generator side is designed for connection to a monopolar output of a high-frequency AC generator. The electrical terminal element on the connecting device side is designed for connection to an electrical terminal of a connecting device according to the invention as described above. The bridge is designed for electrical bridging of the first electrical contact and the second electrical contact of the electrical terminal.

The electrical terminal element on the generator side is designed to establish a mechanical, for example frictional, and electrical connection to the monopolar output from the generator.

The electrical terminal element on the connecting device side is designed to establish a mechanical, for example frictional, and electrical connection to the electrical terminal of the connecting device. More particularly, the electrical terminal element on the connecting device side may be designed as a common socket that can be pushed onto the electrical terminal designed as a common plug. Alternatively, the electrical terminal element on the connecting device side may be designed as a common plug that can be inserted into the electrical terminal in the form of a common socket.

The bridge connects the one pole of the monopolar output of the generator to both contacts of the electrical terminal of the connecting device. For this purpose, the bridge bridges the contacts of the electrical terminal of the connecting device that are isolated from one another (via the contact insulation).

The monopolar cable can be used for monopolar operation of a surgical instrument operable in a monopolar and bipolar manner, comprising the connecting device of the invention. Changing from bipolar operation to monopolar operation requires merely connection of the monopolar cable rather than a bipolar cable to the electrical terminal of the connecting device of the invention, and connection to the monopolar output of the generator. It is thus advantageously possible to avoid a complex change of instruments during a surgical intervention.

In one development, the bridge is designed in an arrangement in the electrical terminal element on the generator side, in the electrical terminal element on the connecting device side or in a region along the monopolar cable between the electrical terminal element on the generator side and the electrical terminal element on the connecting device side.

If the bridge is formed in the electrical terminal element on the generator side, two electrical wires are electrically connected to the bridge. The two electrical wires run in isolation from one another along the monopolar cable as far as the electrical terminal element on the connecting device side. The electrical terminal element on the connecting device side forms mutually separate electrical contact with the first contact and the second contact of the electrical terminal of the connecting device.

If the bridge is formed in the region along the monopolar cable, one electrical wire is electrically connected along the monopolar cable from the electrical terminal element on the generator side to the bridge, and two electrical wires are electrically connected from the bridge to the electrical terminal element on the connecting device side. The two electrical wires run in isolation from one another. The electrical terminal element on the connecting device side forms mutually separate electrical contact with the first contact and the second contact of the electrical terminal of the connecting device.

The bridge is preferably formed in the electrical terminal element on the connecting device side. In this case, an electrical wire runs along the monopolar cable from the electrical terminal element on the generator side to the electrical terminal element on the connecting device side. The electrical terminal element on the connecting device side forms common electrical contact with the first contact and the second contact of the electrical terminal of the connecting device.

The monopolar cable according to the invention with a bridge, especially in the electrical terminal element on the connecting device side, reliably connects the first contact and the second contact to the one pole of the monopolar output of the generator.

Further, a surgical instrument, especially for high-frequency surgery, comprises a connecting device according to the invention as described above and an accessory operable in a monopolar and additionally or alternatively bipolar manner. The accessory operable in a monopolar and additionally or alternatively bipolar manner is coupled electrically and mechanically to the connecting device via the accessory coupling of the connecting device.

In one development of the present invention, the connecting device is designed as a handle, especially as a movable handle with an actuating element for actuating an accessory coupled thereto, preferably in the form of a clamp or shears.

All developments already described above are also transferable or applicable to the surgical instrument according to the invention. All the advantages mentioned are likewise correspondingly applicable to the surgical instrument according to the invention.

Additionally, a surgical system, especially for high-frequency surgery, comprises a surgical instrument according to the invention as described above, a high-frequency generator (HF generator), and a monopolar cable according to the invention as described above. The HF generator has at least one monopolar output. The monopolar cable is connected by the electrical terminal element on the connecting device side, to the electrical terminal of the connecting device of the surgical instrument, and by the electrical terminal element on the generator side to the monopolar output of the HF generator. The accessory of the surgical instrument is connected in a monopolar manner via the connecting device and the connected monopolar cable to the monopolar output of the HF generator.

All developments already described above are also transferable or applicable to the surgical system according to the invention. All the advantages mentioned are likewise correspondingly applicable to the surgical system according to the invention.

The above configurations and developments can, if viable, be combined with one another as desired. Further possible configurations, developments and implementations of the invention also include combinations that have not been excessively specified of the features of the invention that are described above or hereinafter with regard to the working examples. More particularly, the person skilled in the art will also add on individual aspects as improvements or additions to the respective basic form of the present invention.

The appended figures are intended to impart further understanding of the embodiments of the invention. They illustrate embodiments and, in association with the description, serve to elucidate principles and concepts of the invention. Other embodiments and many of the advantages mentioned are apparent with regard to the drawings. The elements of the drawings are not necessarily shown true to scale with respect to one another.

In the figures elements, features and components that are the same, have the same function and the same effect—unless stated otherwise—are each given the same reference numerals.

The present invention is elucidated in detail hereinafter with reference to the working examples given in the schematic figures of the drawing.

DETAILED DESCRIPTION OF REPRESENTATIVE EMBODIMENTS

Figure 1:
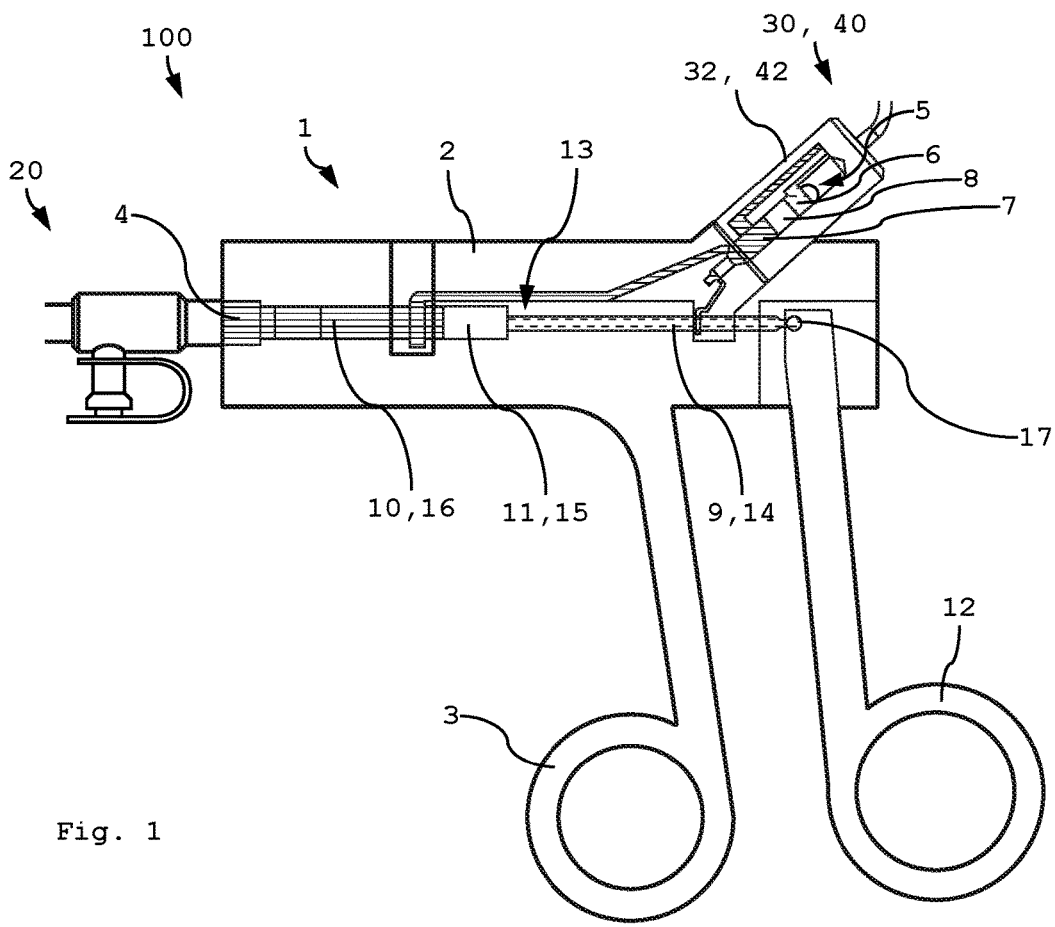
FIG. 1 shows a working example of a surgical instrument with a connected bipolar cable.
Figure 2:
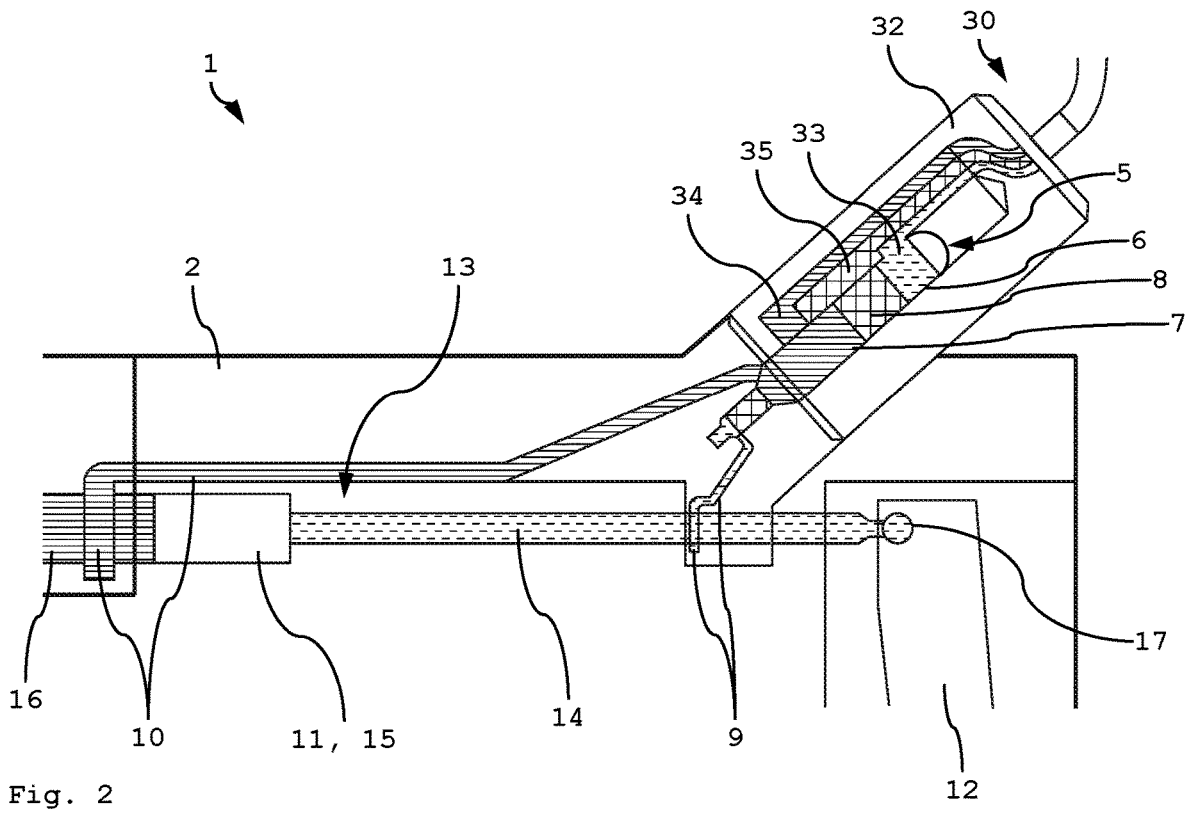
FIG. 2 is an enlarged detail view from FIG. 1.
Figure 3:
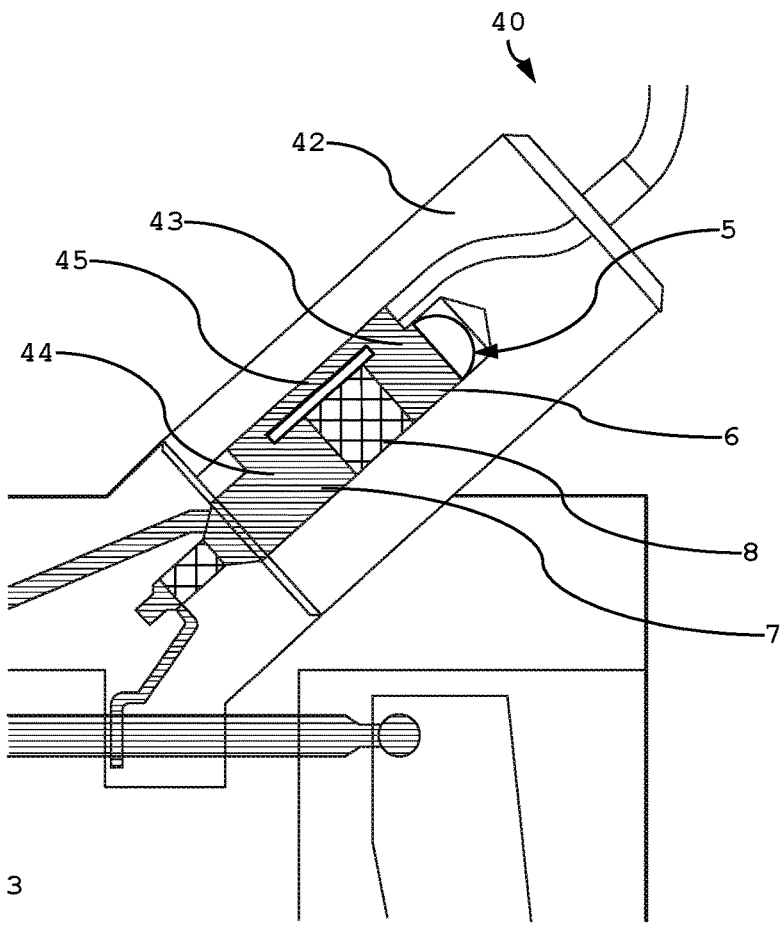
FIG. 3 is an enlarged detail view of the working example of the surgical instrument from FIG. 1 with a connected monopolar cable.

FIGS. 1 to 3 illustrate a schematic of a first working example of a surgical instrument 100 with a connected of bipolar cable 30, or of the monopolar cable 40.

The surgical instrument comprises a working example of a connecting device 1 and an accessory 20.

The accessory 20 here is an accessory operable in a monopolar and bipolar manner. It is of course also possible to connect an accessory operable solely in a monopolar manner or solely in a bipolar manner to the surgical instrument 100.

The connecting device 1 takes the form of a handle and comprises a housing 2 with a distal grip limb 3 (remote from the user/surgeon and facing a patient's body), an accessory coupling 4, an electrical terminal element 5 with a first contact 6, a second contact 7, a contact insulation 8, a first power lead 9, a second power lead 10, a lead insulation 11, an actuating element 12 designed as a proximal grip limb (facing the user/surgeon and remote from a patient's body), and a drive 13.

The accessory coupling 4 is disposed at a distal end of the connecting device. It is designed for detachable mechanical and electrical connection of the accessory 20 to the connecting device 1. The accessory coupling 4 is designed here by way of example as a ring sprung in radial direction, which can snap into, or is snap-fittable with, a groove on the outer surface of a shaft of a tool.

The electrical terminal element 5 is disposed at a proximal end of the connecting device 1 and is designed as a common plug. The common plug of the terminal element 5 here, by way of example, has an essentially cylindrical shape with circular cross section and an outer surface that extends over the outside of the cylindrical form. In a first region, the proximal region here, the first contact 6 is disposed on the outer surface of the common plug of the electrical terminal element 5. In a second region, the distal region here, the second contact 7 is disposed on the outer surface of the common plug of the electrical terminal element 5. The first contact 6 and the second contact 7 each have an electrical connection toward the distal end of the common plug of the electrical terminal element 5. The first contact 6 and the second contact 7 and the electrical connections thereof are electrically insulated from one another by the contact insulation 8 along the common plug of the electrical terminal element 5.

The contact insulation 8 is designed such that, in monopolar or bipolar operation at an AC current with a voltage of up to 5.5 kV, no short circuit or flashover can occur between the first contact 6 and the second contact 7 (in bipolar operation) or between these and their environment (in monopolar and bipolar operation). In monopolar operation, the current can flow merely from one or two of the contacts to a neutral electrode provided on the patient.

A cable 30, 40 is electrically connected, and detachably mechanically connected, to the common plug of the terminal element 5 via a suitable connecting element 32, 42 on the connecting device side. For this purpose, the electrical connecting element 32, 42 on the connecting device side is designed as a fitting common socket and is pushed onto the common plug of the terminal element 5.

The first power lead 9 electrically connects the first contact 6 by a part of the accessory coupling 4 that is movable by means of a drive rod 14. Part of the first power lead 9 is formed here by the drive rod 14 of the drive 13.

The second power lead 10 electrically connects the second contact 7 to a fixed part of the accessory coupling 4. Part of the second power lead 10 is formed here by a sliding sleeve 16 of the drive 13.

The first power lead and the second power lead are electrically insulated from one another and at least partly from their environment by the lead insulation 11. Part of the lead insulation 11 is formed here by a sliding sleeve 15 of the drive 13. The lead insulation 11 is designed such that, in monopolar or bipolar operation at an AC current with a voltage of up to 5.5 kV, no short circuit or flashover can occur between the first power lead 9 and the second power lead 10 (in bipolar operation) or between these and their environment (in monopolar and bipolar operation).

The actuating element 12 is designed as a proximal grip limb of the actuating element. The proximal grip limb 12 is rotatably mounted in the housing 2 and may be turned/rotated or pivoted relative to the distal grip limb 3. By means of the proximal grip limb of the actuating element 12, it is thus possible to transmit a torque or rotary movement to the drive 13.

The drive 13 comprises the drive rod 14 and a sliding sleeve 15 with sliding sleeve 16 disposed thereon.

The drive rod 14 is mounted in the sliding sleeve 15 so as to be movable translationally in the direction toward the accessory coupling 4 with respect to the housing 2. By means of a sliding surface 17 at its proximal end, the drive rod 14 is mechanically connected to the proximal grip limb of the actuating element 12. The drive rod 14 extends up to the accessory coupling 4, such that it can transmit a force or translation there to a mechanism (not shown here) of the coupled-on accessory 20.

The sliding sleeve 15 firstly provides the slide mounting for the drive rod 14 with respect to the housing 2 and secondly part of the lead insulation 11. For this purpose, the sliding sleeve 15 is surrounded by the sliding sleeve 16 at its outer surface. The sliding sleeve 15 may be manufactured from a plastic, especially a friction-reducing and preferably steam-sterilizable plastic such as PEEK, polytetrafluoroethylene (PTFE) and the like. The guide sleeve of the sliding surface 17 contains an electrically conductive material, preferably stainless steel, gold, platinum, copper, aluminium or the like, especially gold-coated stainless steel. As a result, the drive rod 14 is movable in a linear manner with a low sliding friction within the sliding sleeve 15, and is additionally electrically insulated with respect to the second power lead 10 and the electrically conductive guide sleeve of the sliding surface 17.

By means of the sliding surface 17, a torque or rotary motion or rotation of the proximal grip limb of the actuating element 12 is transmitted to the drive rod 14 and converted to a translational force or translational movement or translation. The drive rod 14 transmits the force or translation to the mechanism of the coupled-on accessory 20.

Thus, as well as the mechanical connection to the housing 2 on the accessory coupling 4, firstly an electrical connection is established between the accessory 20 coupled to the housing 2 and the first contact 6 and the second contact 7, and secondly a mechanical connection between the mechanism of the accessory 20 and the drive 13.

FIG. 2 shows a schematic diagram of an enlarged detail of the surgical instrument according to FIG. 1 with a connected bipolar cable 30.

In the embodiment shown, the bipolar cable 30 has been pushed onto the common plug of the terminal element 5 by an electrical terminal element of the connecting element 32 on the connecting device side in the form of a common socket. In further embodiments, the common plug of the terminal element 5 may additionally be surrounded by a plug sleeve 18, not shown here for better clarity (see FIG. 5), with greater internal diameter compared to the terminal element of the connecting element 32, which protects the plug of the terminal element 5 and is designed to accommodate the connecting element 32 of the bipolar cable in the form of a common socket.

The common socket of the connecting element 32 has a hole in essentially cylindrical form with circular cross section, designed to accommodate the common plug of the terminal element 5. The common socket of the connecting element 32 together with the common plug of the terminal element 5 forms a transition fit or an interference fit, such that sufficient static friction for detachable mechanical connection exists between the two. Additionally or alternatively, the mechanical connection may be established by means of an O-ring or a radially sprung (snap) ring between the common socket of the connecting element 32 and the common plug of the terminal element 5.

In a proximal region of the common socket of the connecting element 32, a first cable contact 33 is arranged along the internal circumference of the hole. In a distal region of the common socket of the connecting element 32, a second cable contact 34 is arranged along the inner circumference of the hole. A cable contact insulation 35 is arranged between the first cable contact 33 and the second cable contact 34, which electrically isolates the first cable contact 33 from the second cable contact 34.

When the common socket of the connecting element 32 has been pushed onto the common plug 5, there is a detachable mechanical connection between the bipolar cable 30 and the connecting device 1. In addition, the first cable contact 33 exclusively adjoins the first contact 6, and the second cable contact 34 exclusively adjoins the second contact 7, such that there is an electrical connection between these in each case.

The surgical instrument 100 can be operated in a bipolar manner via the connected bipolar cable 30.

FIG. 3 shows a schematic of an enlarged detail of the surgical instrument of FIG. 1 with a connected monopolar cable 40 according to one working example. All that are elucidated hereinafter are the differences from the bipolar cable 30 from FIG. 2. The rest is as described above in relation to FIG. 2.

The monopolar cable 40 has been pushed onto the common plug 5 by its electrical terminal element 42 on the connecting device side, in the form of a common socket. The common socket 42 has a hole in essentially cylindrical form with a circular cross section. The common socket 42 together with the common plug 5 forms a transition fit or an interference fit, such that sufficient static friction for detachable mechanical connection exists between the two. Additionally or alternatively, the mechanical connection can be established via an O-ring or radially sprung (snap) ring between the common socket 42 and the common plug 5.

A first cable contact 43 is arranged in a proximal region of the common socket 42 along the inner circumference of the hole. A second cable contact 44 is arranged in a distal region of the common socket 42 along the inner circumference of the hole. A bridge 45 is arranged between the first cable contact 43 and the second cable contact 44, which electrically bridges the first cable contact 43 and the second cable contact 44. Alternatively, it is also possible for just a single elongated cable contact that extends over the entire area of the first and second cable contacts 43, 44 to be disposed within the hole.

When the common socket 42 has been pushed onto the common plug 5, there is a detachable mechanical connection between the monopolar cable 40 and the connecting device 1. In addition, the first cable contact 43 exclusively adjoins the first contact 6, and the second cable contact 44 exclusively adjoins the second contact 7, such that the two contacts 6, 7 are bridged via the bridge 45 and the two cable contacts 43, 44 of the monopolar cable 40.

The surgical instrument 100 can be operated in a monopolar manner via the connected monopolar cable 40.

FIGS. 4 to 7 show a schematic of a further working example of the surgical instrument 100 according to the present invention, corresponding essentially to the working example of FIGS. 1 to 3. All that are elucidated hereinafter are differences from the working example of FIGS. 1 to 3. The rest is accordingly applicable to the details given in relation to FIGS. 1 to 3 above.

The common plug of the terminal element 5 additionally has a plug sleeve 18 that surrounds the cylindrical common plug of the terminal element 5 at a predefined radial distance. The plug sleeve 18 protects the common plug of the terminal element 5 from mechanical deformation and facilitates the pushing of a common socket of a cable onto the common plug of the terminal element 5 by virtue of its guiding properties. In addition, an O-ring or radially sprung (snap) ring may be provided, which increases the friction between the common socket and the common plug of the terminal element 5 or the plug sleeve 18.

The accessory 20 is executed here as a clamp. The clamp 20 comprises a mechanism 21 and a manipulator 22 formed here by two clamp jaws. The clamp jaws can be turned toward one another and away from one another again via the mechanism 21. The mechanism 21 is mechanically connected to the accessory coupling 4 by the drive 13, especially by the drive rod 14. The drive rod 14 transmits a torque or rotary movement as translational force or translation to the mechanism 21. The mechanism 21 converts the translational force or translation to a torque or rotary movement and transmits said torque or rotary movement to the clamp jaws of the manipulator 22.

Figure 4:
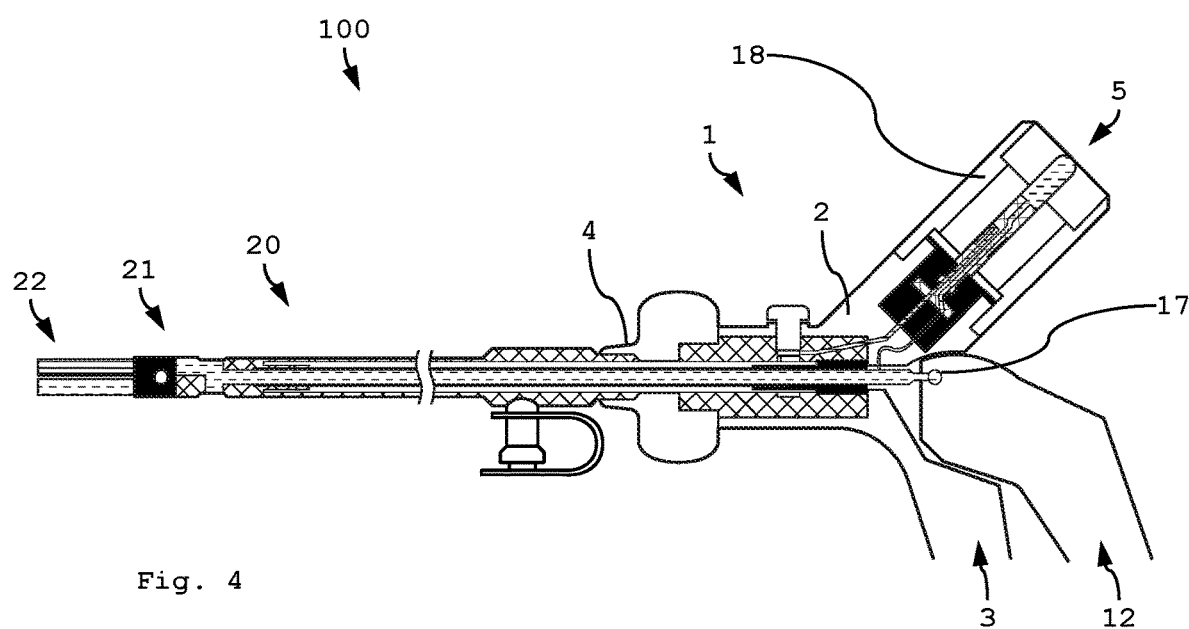
FIG. 4 shows a section view of a working example of a surgical instrument.
Figure 5:
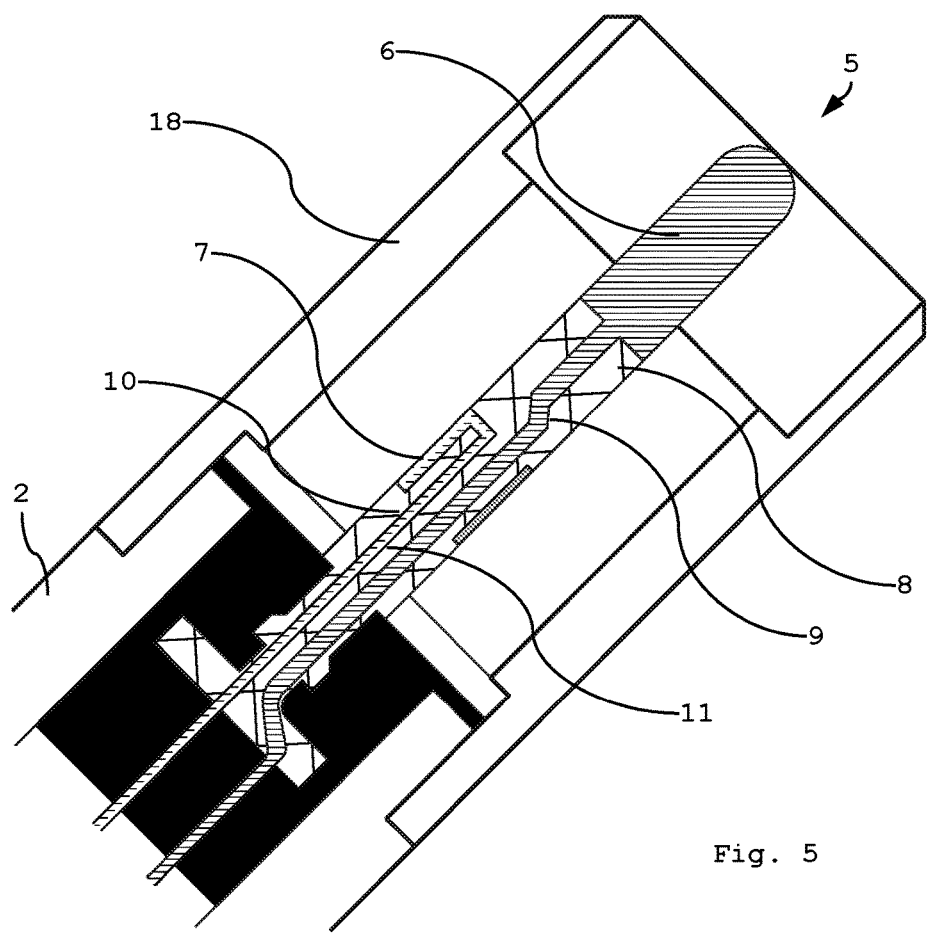
FIG. 5 is an enlarged detail view from FIG. 4.

FIG. 5 shows a schematic of an enlarged detail of the surgical instrument of FIG. 4.

The common plug of the terminal element 5 here is protected within the plug sleeve 18, which is mechanically connected in a detachable or fixed manner to the housing 2. The plug sleeve 18 may also be executed in an integral or one-piece manner with the housing 2. In further embodiments, a plug sleeve 18 in a grip limb, preferably the immobile grip limb 3, would also be conceivable.

Figure 6:
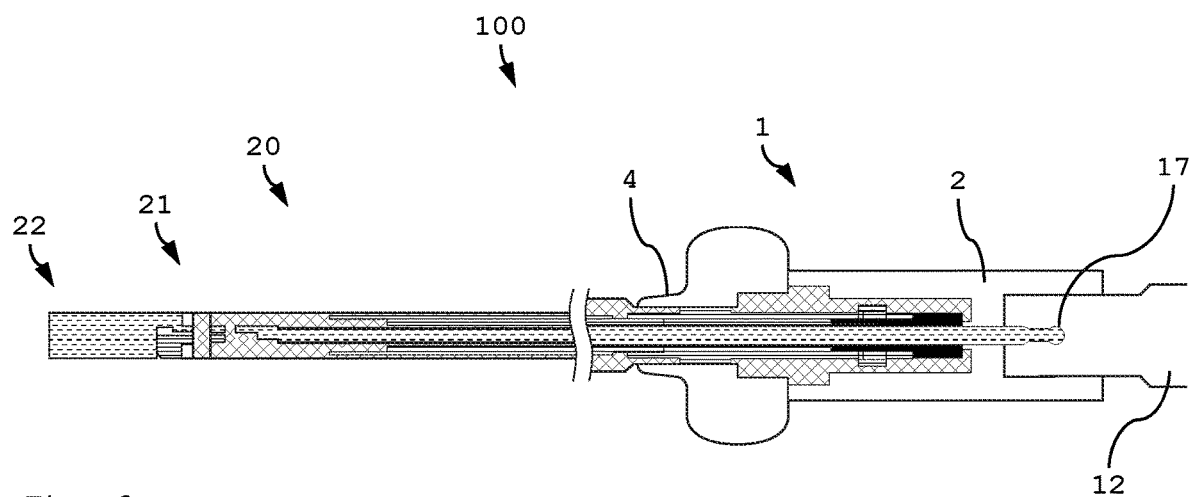
FIG. 6 shows a further section view of the surgical instrument from FIG. 4.

FIG. 6 shows a schematic of the surgical instrument of FIG. 4 in a section plane at right angles to that of FIG. 4.

A torque or rotary movement of the proximal grip limb of the actuating element 12 is transmitted to the drive rod 14 at the sliding surface 17. The interplay of sliding surface 17 and drive rod 14 translationally guided within the sliding sleeve 15 converts the torque or rotary movement to a translational force or translation.

Figure 7:
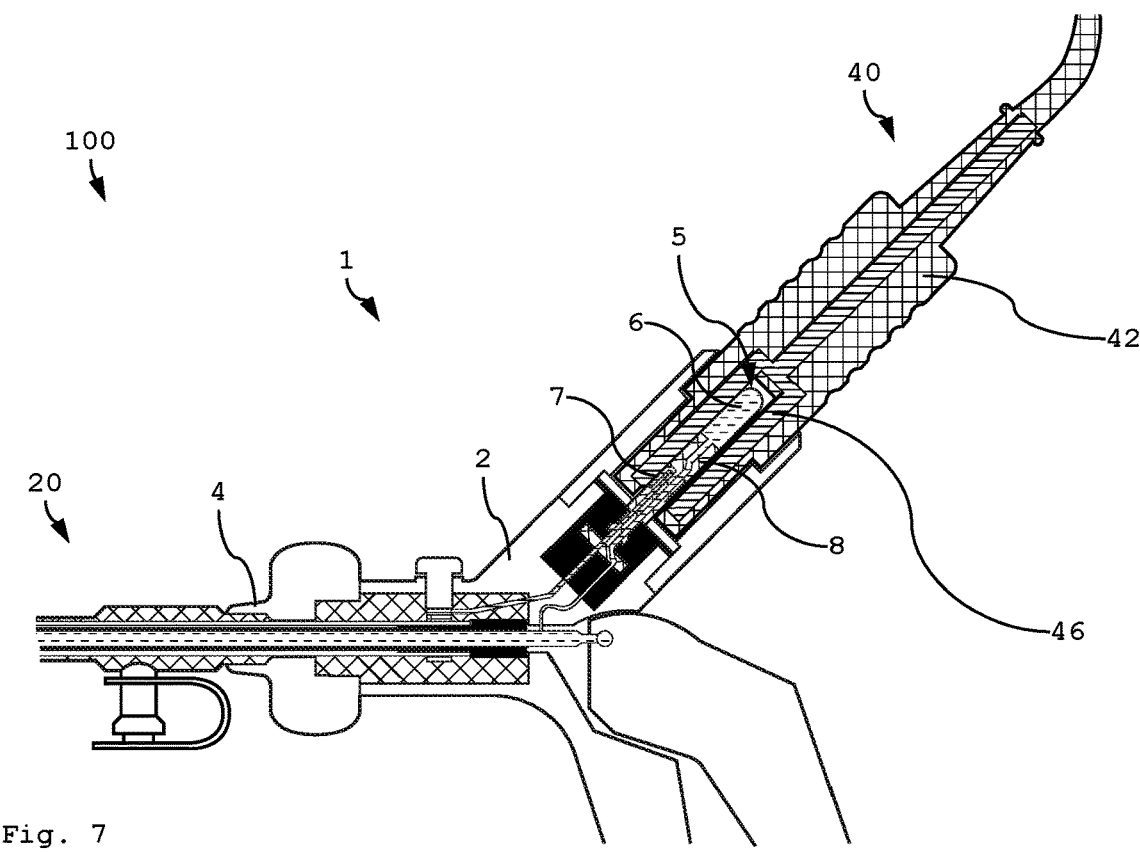
FIG. 7 illustrates the surgical instrument from FIG. 4 with a connected monopolar cable according to a working example.

In FIG. 7, the surgical instrument of FIG. 4 with a connected monopolar cable 40 is shown in schematic form in a further working example, corresponding essentially to the working example of FIG. 3. All that are elucidated hereinafter are differences from the working example of FIG. 3. The rest is as described above in relation to FIG. 3.

Rather than two cable contacts with a bridge (cf. FIG. 3), the monopolar cable 40 has just a single elongated cable contact 46 in the electrical terminal element 42 on the connecting device side in the form of a common socket. The cable contact 42 electrically connects and hence bridges the first contact 6 and the second contact 7.

Figure 8:
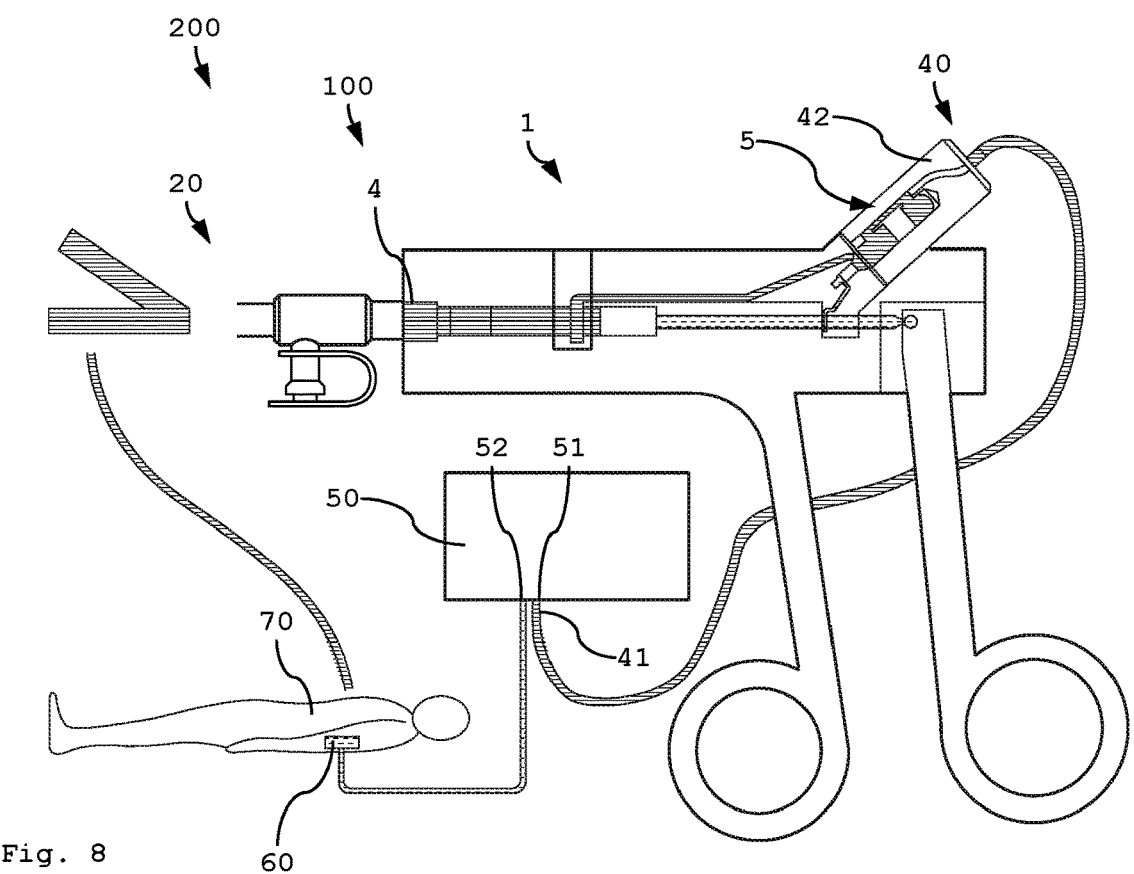
FIG. 8 shows a working example of a surgical system.

FIG. 8 shows a schematic of a working example of a surgical system 200.

The surgical system 200 comprises the surgical instrument 100 according to FIGS. 1 to 3 or 4 to 7, the monopolar cable 40 according to FIG. 3 or 7, a high-frequency generator (HF generator) 50 and a counterelectrode or neutral electrode 60.

The monopolar cable 40 is connected to a monopolar output 51 of the HF generator 50 by an electrical terminal element 41 on the generator side. The electrical terminal element of the connecting element 42 on the connecting device side connects the monopolar cable 40 to the common plug of the terminal element 5 of the connecting device 1 of the surgical instrument 100. The first contact and the second contact of the common plug of the terminal element 5 are bridged by the bridge of the monopolar cable 40 and electrically connected to the one pole of the HF generator 50. The accessory 20 of the surgical instrument 100 is connected mechanically and electrically to the connecting device 1 via the accessory coupling 4 of the connecting device 1. The accessory 20 here is electrically connected to the one pole of the HF generator 50 via the connecting device 1.

The counterelectrode 60 is connected via a monopolar cable to a counterelectrode output 52 of the HF generator 52 and mounted on a patient 70, for example in the form of an adhesive electrode. Thus, the counterelectrode 60 or the patient 70 is electrically connected to an opposite pole of the HF generator 50.

A surgeon can use the surgical instrument 100 operated in a monopolar manner by the generator via the monopolar cable 40 in a surgical intervention to cut tissue in the patient 70 with monopolar AC current between the accessory 20 and the counterelectrode 60 (electrotomy) and simultaneously or alternatively to stem bleeding (coagulation).

Changing to bipolar operation during the surgical intervention requires merely, rather than the monopolar cable 40, a bipolar cable with its electrical terminal element on the connecting device side to be pushed onto the common plug 5, and to be connected by its electrical terminal element on the generator side to a bipolar output of the HF generator 50.

Even though the present invention has been described in full above with reference to preferred working examples, it is not limited thereto, but is modifiable in various ways.

For example, rather than a bridge in the monopolar cable, it is also possible for bridging by a switchable bridge to be provided in the connecting device or in the HF generator (for example by means of a switch in the connecting device and/or in the HF generator).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein. Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A connecting device for surgical instruments operable in a monopolar manner and bipolar manner, for high-frequency surgery, the connecting device comprising:
   a housing;
   an accessory coupling disposed on the housing and configured for mechanical and electrical coupling of an accessory operable in a monopolar and/or bipolar manner; and
   an electrical terminal that is disposed on the housing and has a first contact and a second contact, wherein the electrical terminal is configured to be mechanically and electrically connectable to each of a monopolar cable and a bipolar cable, wherein the electrical coupling is configured such that, when connected to a monopolar cable, the first contact and the second contact are configured to both be in direct electrical connection with a same electrical contact of the monopolar cable; and wherein the electrical coupling is configured such that, when connected to a bipolar cable, the first contact is configured to only be in direct electrical connection with a first electrical contact of the bipolar cable and to not be in electrical connection with a second electrical contact of the bipolar cable and the second contact is configured to only be in direct electrical connection with the second electrical contact of the bipolar cable and to not be in electrical connection with the first electrical contact of the bipolar cable, and wherein the first contact and the second contact are configured to be electrically connected to the accessory coupling and isolated in such a way that an accessory coupled by the accessory coupling is operable in a monopolar manner, with an electrical connection of the accessory to both the first contact and the second contact and in a bipolar manner with an electrical connection of the accessory to the first contact isolated from an electrical connection of the accessory to the second contact.

2. The connecting device of claim 1, further comprising a contact insulation for electrical isolation of the first contact and of the second contact from one another.

3. The connecting device of claim 2, wherein a first power lead for electrical connection of the first contact and a second power lead for electrical connection of the second contact to the accessory coupling are disposed in or on the housing, and further comprising a lead insulation for electrical isolation of the first power lead and of the second power lead from one another and from the environment thereof.

4. The connecting device of claim 3, wherein the contact insulation and/or the lead insulation has an isolation gap configured for AC currents in monopolar operation.

5. The connecting device of claim 4, wherein the electrical terminal is configured for optional connection of the first contact and of the second contact to a monopolar cable or to a bipolar cable via a common plug.

6. The connecting device of claim 5, wherein the electrical terminal is adapted as the common plug and has, on its outer surface, in its longitudinal direction, the first contact in a first contact region, the contact insulation in an insulation region, and the second contact in a second contact region.

7. The connecting device of claim 5, wherein the electrical terminal takes the form of a common socket, and on its inner surface, in its longitudinal direction, has the first contact in a first contact region, the contact insulation in an insulation region, and the second contact in a second contact region.

8. The connecting device of claim 3, wherein the contact insulation and/or the lead insulation each have an isolation gap configured for AC currents with a voltage of up to 5.5 kV [kilovolts].

9. The connecting device of claim 1, further comprising an actuating element disposed on the housing, and a drive disposed in or on the housing, the drive being mechanically coupled to the actuating element, and wherein the drive is configured to transmit a movement of the actuating element to a mechanism of an accessory that is mechanically connectable via the accessory coupling.

10. The connecting device of claim 9, wherein the drive is configured so as to be at least partly electrically conductive and forms at least partly either the first power lead and/or the second power lead.

11. The connecting device of claim 9, wherein the accessory coupling is configured for mechanical and electrical coupling of an accessory in the form of a clamp or shears.

12. The connecting device of claim 10, wherein the accessory coupling is configured for mechanical and electrical coupling of an accessory in the form of a clamp or shears.

13. A surgical instrument for high-frequency surgery, the surgical instrument comprising:
a connecting device, the connecting device comprising a housing, an accessory coupling disposed on the housing and configured for mechanical and electrical coupling of an accessory operable in a monopolar manner and/or bipolar manner, and an electrical terminal that is disposed on the housing and has a first contact and a second contact, wherein the electrical terminal is configured to be mechanically and electrically connectable to each of a monopolar cable and a bipolar cable, wherein the electrical coupling is configured such that, when connected to a monopolar cable, the first contact and the second contact are configured to both be in direct electrical connection with a same electrical contact of the monopolar cable; and wherein the electrical coupling is configured such that, when connected to a bipolar cable, the first contact is configured to only be in direct electrical connection with a first electrical contact of the bipolar cable and to not be in direct electrical connection with a second electrical contact of the bipolar cable and the second contact is configured to only be in direct electrical connection with the second electrical contact of the bipolar cable and to not be in electrical connection with the first electrical contact of the bipolar cable, and wherein the first contact and the second contact are configured to be electrically connected to the accessory; and the accessory, coupled electrically and mechanically to the connecting device via the accessory coupling of the connecting device is operable in a monopolar manner with an electrical connection of the accessory to both the first contact and the second contact and in a bipolar manner with an electrical connection of the accessory to the first contact isolated from an electrical connection of the accessory to the second contact.

14. The surgical instrument of claim 13, wherein the connecting device is configured as a handle.

15. The surgical instrument of claim 14, wherein the handle is a movable handle with an actuating element for actuating an accessory coupled thereto.

16. The surgical instrument of claim 13, further comprising:
an HF generator having at least one monopolar output; and
a monopolar cable connected by an electrical terminal element on a connecting device side to the electrical terminal of the connecting device of the surgical instrument and by an electrical terminal element on the generator side to the monopolar output of the HF generator, wherein the monopolar cable comprises the cable electrical terminal element on the generator side, which is configured for connection to the monopolar output of the HF generator, and the electrical terminal element on the connecting device side, which is configured for connection to the electrical terminal of the connecting device, and a bridge configured for electrical bridging of the first electrical contact and the second electrical contact of the electrical terminal, wherein the accessory of the surgical instrument is connected in a monopolar manner via the connecting device and the connected monopolar cable to the monopolar output of the HF generator.

17. The surgical instrument of claim 16, wherein the bridge is formed either in the electrical terminal element on the generator side, in the electrical terminal element on the connecting device side or in a region along the monopolar cable between the electrical terminal element on the generator side and the electrical terminal element on the connecting device side.

18. A monopolar cable for surgical instruments operable in a monopolar and bipolar manner, especially for high-frequency surgery, comprising:
an electrical terminal element on a generator side, configured for connection to a monopolar output of a high-frequency AC generator; and
an electrical terminal element on the connecting device side, configured for connection to an electrical terminal of a connecting device, wherein the connecting device comprises a housing, an accessory coupling disposed on the housing and configured for mechanical and electrical coupling of an accessory operable in a monopolar and/or bipolar manner, an electrical terminal that is disposed on the housing and has a first contact and a second contact, wherein the electrical terminal is configured to be connectable either to the monopolar cable, wherein the first contact and the second contact are configured to both be in direct electrical connection with a same electrical contact of the monopolar cable or to the bipolar cable, wherein the first contact is configured to only be in direct electrical connection with a first electrical contact of the bipolar cable and to not be in electrical connection with a second electrical contact of the bipolar cable and the second contact is configured to only be in direct electrical connection with the second electrical contact of the bipolar cable and to not be in electrical connection with the first electrical contact of the bipolar cable, and wherein the first contact and the second contact are configured to be electrically connected to the accessory coupling and isolated in such a way that an accessory coupled by the accessory coupling is operable in a monopolar manner with a direct electrical connection of the accessory to both the first contact and the second contact and in a bipolar manner, with a direct electrical connection of the accessory to the first contact isolated from a direct electrical connection of the accessory to the second contact via a bridge configured for electrical bridging of the first electrical contact and the second electrical contact of the electrical terminal.

19. The monopolar cable of claim 18, wherein the bridge is formed either in the electrical terminal element on the generator side, in the electrical terminal element on the connecting device side or in a region along the monopolar cable between the electrical terminal element on the generator side and the electrical terminal element on the connecting device side.

\* \* \* \* \*